(12) United States Patent
Felix et al.

(10) Patent No.: US 11,413,129 B2
(45) Date of Patent: Aug. 16, 2022

(54) IMPLANTABLE PROSTHESIS

(71) Applicant: Davol Inc., Warwick, RI (US)

(72) Inventors: Augustus Felix, Cranston, RI (US); Talia D'Ambruoso, East Greenwich, RI (US); Cuixiang Qu Spinney, North Attleboro, MA (US); Korel Cudmore, Acushnet, MA (US)

(73) Assignee: Davol Inc., Warwick, RI (US)

( * ) Notice: Subject to any disclaimer, the term of this patent is extended or adjusted under 35 U.S.C. 154(b) by 47 days.

(21) Appl. No.: 16/907,100

(22) Filed: Jun. 19, 2020

(65) Prior Publication Data

US 2021/0393389 A1 Dec. 23, 2021

(51) Int. Cl.
  *A61F 2/00* (2006.01)
(52) U.S. Cl.
  CPC .... *A61F 2/0063* (2013.01); *A61F 2002/0068* (2013.01); *A61F 2250/0089* (2013.01)
(58) Field of Classification Search
  CPC ................. A61F 2/0063; A61F 2/0095; A61F 13/00068; A61F 2002/0068; A61F 2002/0072; A61M 1/90; A61B 2090/3937
  See application file for complete search history.

(56) References Cited

U.S. PATENT DOCUMENTS

| | | |
|---|---|---|
| 2,671,444 A | 3/1954 | Pease |
| 3,559,214 A | 2/1971 | Pangman |
| 3,805,301 A | 4/1974 | Liebig |
| 3,875,928 A | 4/1975 | Angelchik |
| 3,988,411 A | 10/1976 | Capozza |
| 4,345,414 A | 8/1982 | Bornat et al. |
| 4,403,604 A | 9/1983 | Wilkinson |
| 4,441,215 A | 4/1984 | Raster |
| 4,545,082 A | 10/1985 | Hood |

(Continued)

FOREIGN PATENT DOCUMENTS

| | | |
|---|---|---|
| AU | 593 267 B2 | 2/1990 |
| DE | 892 663 C | 10/1953 |

(Continued)

OTHER PUBLICATIONS

U.S. Appl. No. 16/907,091, filed Jun. 19, 2020, Felix et al.

(Continued)

*Primary Examiner* — Mohamed G Gabr
(74) *Attorney, Agent, or Firm* — Wolf, Greenfield & Sacks, P.C.

(57) ABSTRACT

An implantable prosthesis for repairing a defect in a muscle or tissue wall. The prosthesis comprises a body of biologically compatible prosthetic material having a preformed three-dimensional contoured shape that independently assumes a three-dimensional curved shape configured to conform to the muscle or tissue wall. The body may be formed of a mesh fabric employing a knit construction. The body may be configured with one or more mechanical characteristics, individually or in any combination, having defined properties which may enhance the ability of the prosthesis to be handled in a surgical, robotic environment while meeting the performance and physical characteristics for soft tissue repair and reconstruction. One or more visual indicia may be provided to facilitate positioning and/or placement of the prosthesis at the muscle or tissue wall.

16 Claims, 7 Drawing Sheets

(56) References Cited

U.S. PATENT DOCUMENTS

| | | |
|---|---|---|
| 4,555,378 A | 11/1985 | Martin et al. |
| 4,573,999 A | 3/1986 | Netto |
| 4,693,720 A | 9/1987 | Scharnberg |
| 4,728,328 A | 3/1988 | Hughes |
| 4,841,948 A | 6/1989 | Bauer |
| 5,061,277 A | 10/1991 | Carpentier et al. |
| 5,112,352 A | 5/1992 | Novack |
| 5,116,370 A | 5/1992 | Foglietti |
| 5,146,933 A | 9/1992 | Boyd |
| 5,147,398 A | 9/1992 | Lynn et al. |
| 5,236,454 A | 8/1993 | Miller |
| 5,258,000 A | 11/1993 | Gianturco |
| 5,292,328 A | 3/1994 | Hain et al. |
| 5,306,296 A | 4/1994 | Wright et al. |
| 5,356,429 A | 10/1994 | Seare |
| 5,356,432 A | 10/1994 | Rutkow et al. |
| 5,366,460 A | 11/1994 | Eberbach |
| 5,383,477 A | 1/1995 | DeMatteis |
| 5,383,925 A | 1/1995 | Schmitt |
| 5,443,508 A | 8/1995 | Giampapa |
| 5,456,720 A | 10/1995 | Schultz et al. |
| 5,466,258 A | 11/1995 | Rubin |
| 5,584,884 A | 12/1996 | Pignataro |
| 5,593,441 A | 1/1997 | Lichtenstein et al. |
| 5,674,279 A | 10/1997 | Wright et al. |
| 5,676,146 A | 10/1997 | Scarborough |
| 5,695,525 A | 12/1997 | Mulhauser et al. |
| 5,702,459 A | 12/1997 | Hummer et al. |
| 5,716,404 A | 2/1998 | Vacanti et al. |
| 5,716,408 A | 2/1998 | Eldridge et al. |
| 5,725,577 A | 3/1998 | Saxon |
| 5,743,917 A | 4/1998 | Saxon |
| 5,766,246 A | 6/1998 | Mulhauser et al. |
| 5,769,864 A | 6/1998 | Kugel |
| 5,796,462 A | 8/1998 | Roffman et al. |
| 5,865,728 A | 2/1999 | Moll et al. |
| 5,895,424 A | 4/1999 | Steele, Sr. et al. |
| 5,954,767 A | 9/1999 | Pajotin et al. |
| 6,004,333 A | 12/1999 | Sheffield et al. |
| 6,024,763 A | 2/2000 | Lenker et al. |
| 6,042,592 A | 3/2000 | Schmitt |
| 6,066,776 A | 5/2000 | Goodwin et al. |
| 6,066,777 A | 5/2000 | Benchetrit |
| 6,074,419 A | 6/2000 | Healy et al. |
| 6,090,116 A | 7/2000 | D'Aversa et al. |
| 6,096,044 A | 8/2000 | Boyd et al. |
| 6,113,623 A | 9/2000 | Sgro |
| 6,120,434 A | 9/2000 | Kimura et al. |
| 6,120,539 A | 9/2000 | Eldridge et al. |
| 6,162,962 A | 12/2000 | Hinsch et al. |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,214,020 B1 | 4/2001 | Mulhauser et al. |
| 6,224,616 B1 | 5/2001 | Kugel |
| 6,241,768 B1 | 6/2001 | Agarwal et al. |
| 6,258,124 B1 | 7/2001 | Darois et al. |
| 6,264,702 B1 | 7/2001 | Ory et al. |
| 6,267,772 B1 | 7/2001 | Mulhauser et al. |
| 6,270,530 B1 | 8/2001 | Eldridge et al. |
| 6,280,453 B1 | 8/2001 | Kugel et al. |
| 6,287,293 B1 | 9/2001 | Jones et al. |
| 6,287,316 B1 | 9/2001 | Agarwal et al. |
| 6,290,708 B1 | 9/2001 | Kugel et al. |
| 6,306,154 B1 | 10/2001 | Hudson et al. |
| 6,312,442 B1 | 11/2001 | Kieturakis et al. |
| 6,312,456 B1 | 11/2001 | Kranz et al. |
| 6,319,264 B1 | 11/2001 | Tormala et al. |
| 6,368,541 B1 | 4/2002 | Pajotin et al. |
| 6,451,139 B1 | 9/2002 | Weber-Unger et al. |
| 6,610,006 B1 * | 8/2003 | Amid ............... A61F 2/0063 600/37 |
| 6,723,133 B1 | 4/2004 | Pajotin |
| 6,740,122 B1 * | 5/2004 | Pajotin ............... A61F 2/0063 606/151 |
| 9,603,698 B2 | 3/2017 | Kerr et al. |
| 2001/0027347 A1 | 10/2001 | Rousseau |
| 2001/0034528 A1 | 10/2001 | Foerster et al. |
| 2001/0049538 A1 | 12/2001 | Trabucco |
| 2001/0049539 A1 | 12/2001 | Rehil |
| 2001/0053919 A1 | 12/2001 | Kieturakis et al. |
| 2011/0307077 A1 | 12/2011 | Pfeiffer et al. |

FOREIGN PATENT DOCUMENTS

| | | |
|---|---|---|
| DE | 40 13 447 C1 | 2/1992 |
| DE | 92 12 261 U1 | 12/1992 |
| EP | 0 573 273 A2 | 12/1993 |
| EP | 0 592 244 A2 | 4/1994 |
| EP | 0 614 650 A2 | 9/1994 |
| EP | 0 836 838 A1 | 4/1998 |
| EP | 1 145 693 A2 | 10/2001 |
| FR | 2 682 284 A1 | 4/1993 |
| FR | 2 719 993 A1 | 11/1995 |
| FR | 2 735 015 A1 | 12/1996 |
| GB | 2 226 762 A | 7/1990 |
| JP | H05-329165 A | 12/1993 |
| JP | H07-000430 A | 1/1995 |
| WO | WO 92/13500 A1 | 8/1992 |
| WO | WO 95/07666 A1 | 3/1995 |
| WO | WO 96/03091 A1 | 2/1996 |
| WO | WO 96/41588 A1 | 12/1996 |
| WO | WO 99/03422 A1 | 1/1999 |
| WO | WO 00/15141 A1 | 3/2000 |
| WO | WO 00/15142 A1 | 3/2000 |
| WO | WO 00/42943 A1 | 7/2000 |
| WO | WO 01/15625 A1 | 3/2001 |
| WO | WO 01/80773 A1 | 11/2001 |
| WO | WO 02/07648 A1 | 1/2002 |

OTHER PUBLICATIONS

International Search Report and Written Opinion dated Sep. 30, 2021 in connection with International Application No. PCT/US2021/037338.

\* cited by examiner

IMPLANTABLE PROSTHESIS

FIELD OF DISCLOSURE

The present disclosure relates to an implantable prosthesis, and more particularly to an implantable prosthesis for use in soft tissue and muscle wall repair.

BACKGROUND

A defect in a muscle or tissue wall, such as a hernia, is commonly repaired with an implantable prosthesis that is configured to cover and/or fill the defect. In many instances, a flat sheet of an implantable, non-resorbable, flexible mesh material, such as BARD MESH, has been employed for the parietal repair of hernias and eventrations of the abdominal wall. However, a surgeon may experience some difficulty positioning the mesh between the parietal peritoneum and the abdominopelvic wall. The mesh may also fold or wrinkle and be difficult to maintain in position.

Applicant previously developed an implantable prosthesis for repairing a defect in a muscle or tissue wall to alleviate some of these concerns. Several versions of the prosthesis, which are disclosed in U.S. Pat. Nos. 5,954,767, 6,723,133 and 6,740,122, are made of an implantable, nonabsorbable and flexible material that is formed to independently assume a curved shape adapted to conform to the anatomical shape of the wall. The prosthesis includes a body comprised of a first portion having a substantially spherical shape and a second portion joined to the first portion. The second portion may have a substantially conical or spherical shape.

The prosthesis has proven useful and become established in the practice of muscle or tissue wall repair in the inguinofemoral region. The prosthesis is not subject to stresses when deformed and, therefore, has no tendency to shift upon implantation.

Applicant has nevertheless observed that aspects of the prosthesis could be improved.

It is an object of the present disclosure to provide an improved prosthesis for repairing a defect in a muscle or tissue wall.

SUMMARY

In one illustrative embodiment, an implantable prosthesis for repairing a defect in a muscle or tissue wall. The prosthesis comprises a body of biologically compatible prosthetic material having a preformed three-dimensional contoured shape that independently assumes a curved shape configured to conform to the muscle or tissue wall. The body has a ball burst strength of 45 lbs to 52 lbs.

In one illustrative embodiment, an implantable prosthesis for repairing a defect in a muscle or tissue wall. The prosthesis comprises a body of biologically compatible prosthetic material having a preformed three-dimensional contoured shape that independently assumes a curved shape configured to conform to the muscle or tissue wall. The body has a tensile strength of 12.6 lbs to 17.1 lbs in the machine direction and 31.4 lbs to 44.9 lbs in the cross direction.

In one illustrative embodiment, an implantable prosthesis for repairing a defect in a muscle or tissue wall. The prosthesis comprises a body of biologically compatible prosthetic material having a preformed three-dimensional contoured shape that independently assumes a curved shape configured to conform to the muscle or tissue wall. The body has a tear resistance of 7.8 lbs to 12.3 lbs in the machine direction and 7.7 lbs to 12.9 lbs in the cross direction.

In one illustrative embodiment, an implantable prosthesis for repairing a defect in a muscle or tissue wall. The prosthesis comprises a body of biologically compatible prosthetic material having a preformed three-dimensional contoured shape that independently assumes a curved shape configured to conform to the muscle or tissue wall. The body has an elongation at break of 100.3% to 133.7% in the machine direction and 52.6% to 66.4% in the cross direction.

In one illustrative embodiment, an implantable prosthesis for repairing a defect in a muscle or tissue wall. The prosthesis comprises a body of biologically compatible prosthetic material having a preformed three-dimensional contoured shape that independently assumes a curved shape configured to conform to the muscle or tissue wall. The body has a ball burst strength of 45 lbs to 52 lbs, a tensile strength of 12.6 lbs to 17.1 lbs in the machine direction and 31.4 lbs to 44.9 lbs in the cross direction, a tear resistance of 7.8 lbs to 12.3 lbs in the machine direction and 7.7 lbs to 12.9 lbs in the cross direction and an elongation at break of 100.3% to 133.7% in the machine direction and 52.6% to 66.4% in the cross direction.

In one illustrative embodiment, an implantable prosthesis for repairing an inguinal hernia. The prosthesis comprises a body of biologically compatible prosthetic material having a preformed three-dimensional contoured shape that independently assumes a curved shape configured to conform to the inguinal wall. The body is surrounded by an outer peripheral edge and includes an apex relative to the outer peripheral edge. The body includes a depression configured to receive external iliac vessels, the depression extending in a direction from the apex toward the outer peripheral edge. The body includes visual indicia extending along at least a portion of the depression between the apex and the outer peripheral edge.

In one illustrative embodiment, an implantable prosthesis for repairing an inguinal hernia. The prosthesis comprises a body of biologically compatible prosthetic material having a preformed three-dimensional contoured shape that independently assumes a curved shape configured to conform to the inguinal wall. The body is surrounded by an outer peripheral edge and includes an apex relative to the outer peripheral edge. The body includes a rounded ridge extending from the outer peripheral edge to at least the apex. The rounded ridge is configured to be placed along the axis of the inguinal ligament. The body includes visual indicia extending along at least a portion of the rounded ridge between the outer peripheral edge and the apex.

According to one aspect, the body may be formed of a dual bar warp knit mesh produced according to a first bar pattern chain of 4/2 4/6 4/2 6/8 6/4 6/8 and a second bar pattern chain of 6/8 2/0 6/8 4/2 8/10 4/2. The mesh is knitted of a first monofilament having a first diameter and a second monofilament having a second diameter which is greater than the first diameter. The first monofilament is knitted according to the first bar pattern chain and the second monofilament is knitted according to the second bar pattern chain.

According to one aspect, the body may be formed of a knit mesh that includes a plurality of generally polygonal shaped primary pores defined by knitted strands of first filaments. A pair of individual second extend across each primary pore to define a plurality of secondary pores within each primary pore. Each of the pair of second filaments extend substantially parallel to one another. The first filaments having a first diameter and the second filaments having a second diameter which is greater than the first diameter.

DESCRIPTION OF THE DRAWINGS

Various embodiments of the disclosure will now be described, by way of example, with reference to the accompanying drawings, in which.

DETAILED DESCRIPTION

The present disclosure is directed to an implantable prosthesis for repairing a defect in a muscle or tissue wall. The prosthesis comprises a body of biologically compatible prosthetic material having a preformed three-dimensional contoured shape that independently assumes a three-dimensional curved shape configured to conform to the muscle or tissue wall. In this manner, the prosthesis may be collapsed into a reduced configuration, such as a slender cylinder, for delivery to a surgical site. Upon delivery, the prosthesis may independently return to its preformed three-dimensional contoured shape.

The body may be formed of a material that is relatively flexible, thin and light weight and meets the performance and physical characteristics for soft tissue repair and reconstruction procedures. The prosthesis may be used for reinforcing and closing soft tissue defects, and is particularly indicated for chest wall reconstruction and/or the repair of hernias, such as inguinal hernias.

Embodiments of the prosthesis include a body formed of a mesh fabric. The mesh fabric may employ a knit construction that provides relatively large openings or pores to ensure good visibility of the underlying anatomy without sacrificing mechanical properties of the mesh. The porous character of the fabric allows tissue infiltration to incorporate the prosthesis. The knitted fabric is sufficiently strong and structured to prevent or minimize potential pullout of anchoring fasteners, such as sutures, staples, tacks, and the like. The flexible repair fabric may promote an easy reduction in size for entry into the subject. In this manner, the flexible fabric may be collapsed into a slender configuration, such as a roll, which can be supported in, and advanced through, a narrow laparoscopic cannula for use in laparoscopic procedures.

Aspects of the prosthesis are related to enhancing its handling, such as for use in a surgical, robotic environment. The body may be configured with one or more mechanical characteristics, individually or in any combination, having defined properties which may enhance the ability of the prosthesis to be handled in a surgical, robotic environment while meeting the performance and physical characteristics for soft tissue repair and reconstruction.

Aspects of the prosthesis may include one or more visual indicia to facilitate positioning and/or placement of the prosthesis at the muscle or tissue wall. The indicia may include, alphabetic, numeric, alphanumeric and/or other symbols, individually or in any combination, to identify one or more portions of the prosthesis and/or orientations of the prosthesis relative to the muscle or tissue wall at the defect site.

Figure 1:
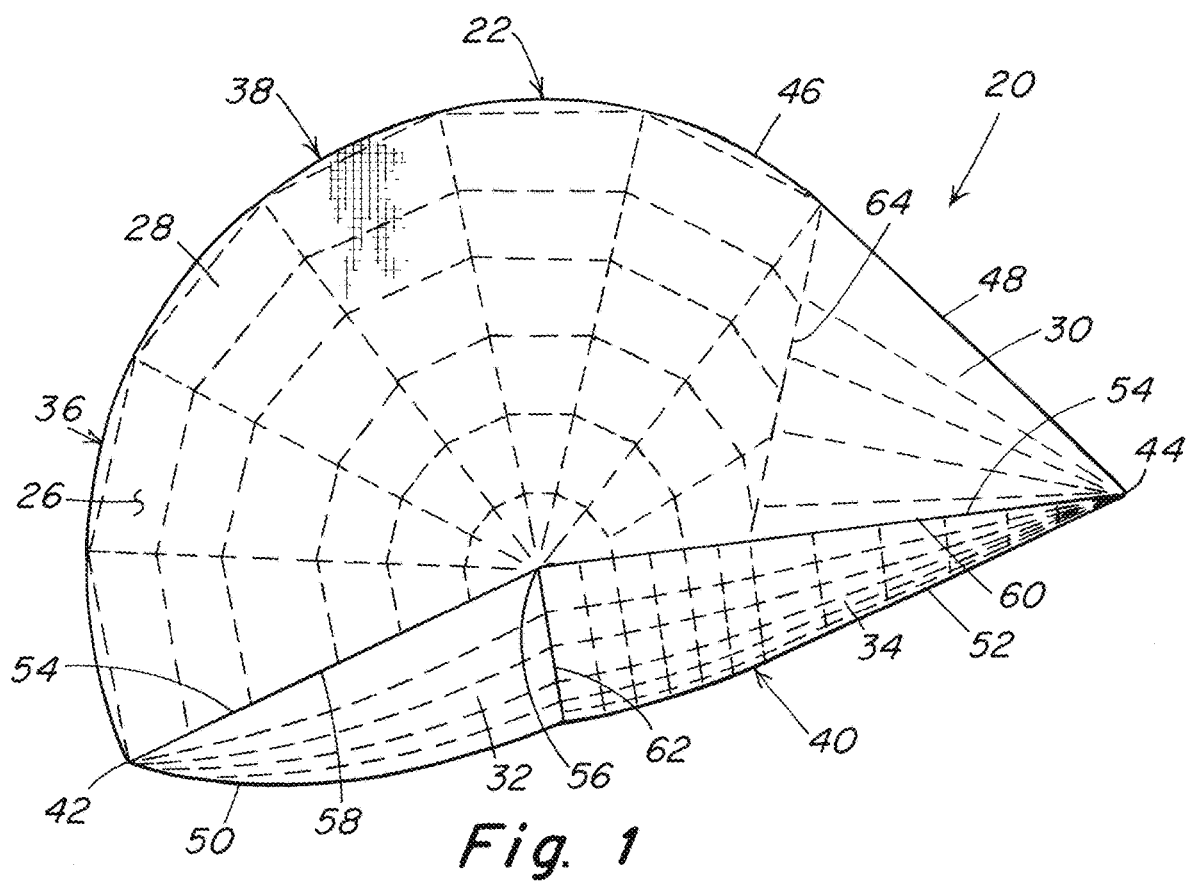
FIG. 1 is a plan view of a prosthesis according to one illustrative embodiment of the disclosure.
Figure 2:
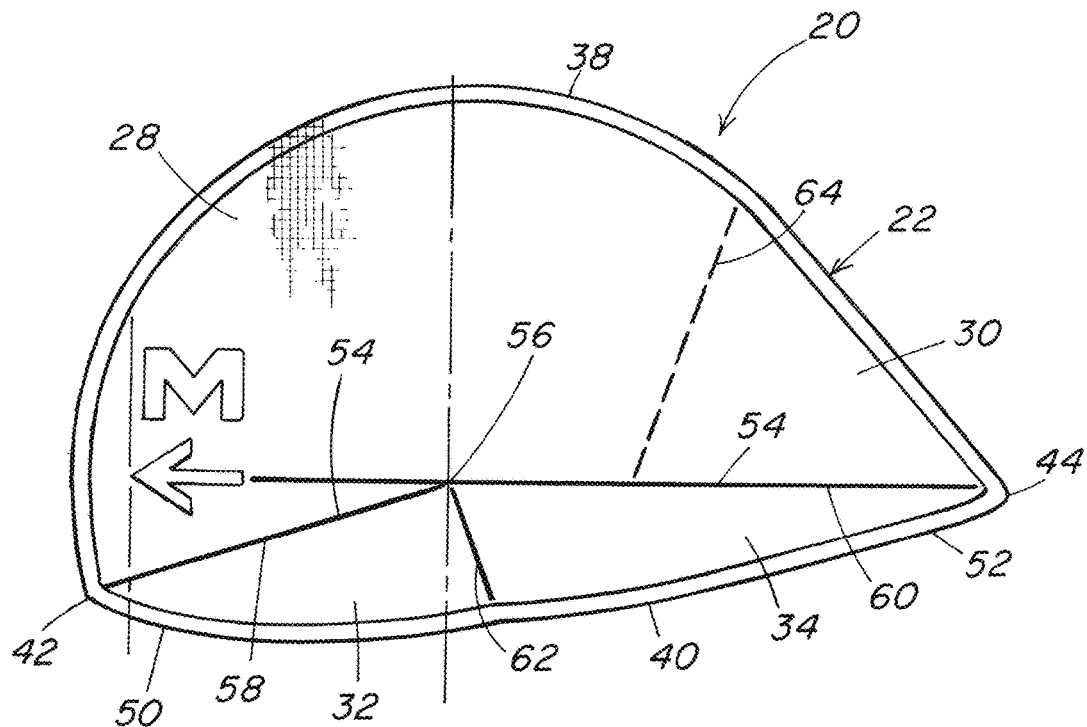
FIG. 2 is a plan view of the prosthesis of FIG. 1 illustrating positioning indicia according to one illustrative embodiment of the disclosure.
Figure 3:
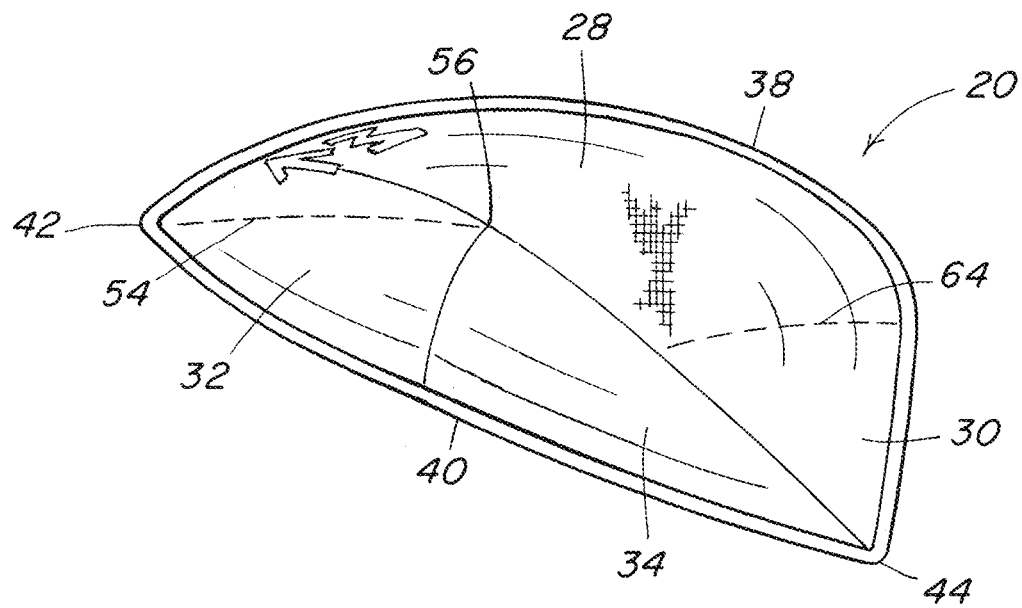
FIG. 3 is a perspective view of the prosthesis of FIGS. 1 and 2.
Figure 5:
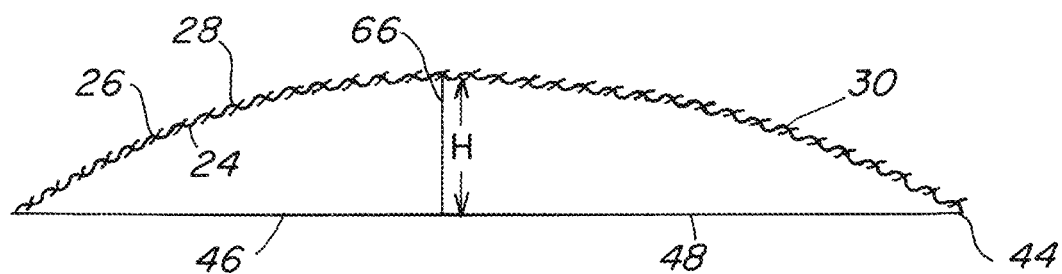
FIG. 5 is a cross-sectional view of the prosthesis taken along section line 5-5 of FIG. 4.
Figure 6:
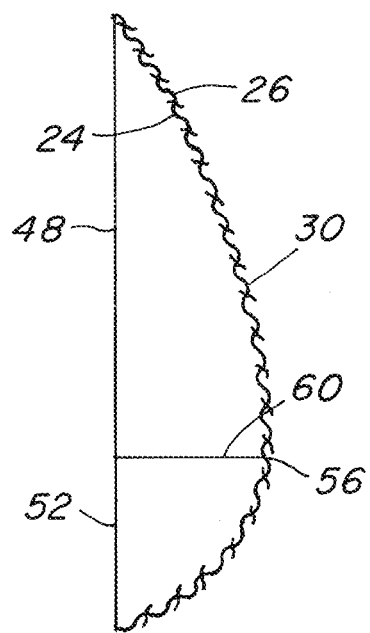
FIG. 6 is a cross-sectional view of the prosthesis taken along section line 6-6 of FIG. 4.

In one illustrative embodiment shown in FIGS. 1-3, the implantable prosthesis 20 includes a body 22 of biocompatible prosthetic material having a preformed three-dimensional contoured configuration with a curved shape configured to conform to the anatomical shape of defective muscle or tissue wall. As illustrated in FIGS. 5-6, the body may include an inner surface 24 formed with an overall generally concave shape and an outer surface 26 formed with an overall generally convex shape. The configuration of the body facilitates placement and minimizes shifting of the prosthesis when positioned on the wall.

The body may a plurality of shaped portions that are formed together or otherwise joined to each other to create a desired configuration. In one embodiment, the body may include a first portion 28, a second portion 30, a third portion 32 and a fourth portion 34. The body may be surrounded by an outer peripheral edge 36 which includes a first margin 38 and a second margin 40 which are joined to each other at first and second ends 42, 44 of the body. The first margin 38 may include a first segment 46 which extends along and defines an outer edge of the first portion 28 and a second segment 48 which extends along and defines an outer edge of the second portion 30. Similarly, the second margin 40 may include a first segment 50 which extends along and defines an outer edge of the third portion 32 and a second segment 52 which extends along and defines an outer edge of the fourth portion 34.

The body may include a first curved surface formed by the first and second portions 28, 30 and a second curved surface formed by the third and fourth portions 32, 34. The first and second surface may be joined to each other along a rounded ridge 54 which extends from the first end 42 to the second end 44 of the body. In one embodiment for repairing an inguinal hernia, the rounded ridge is configured to be placed along the axis of the inguinal ligament.

The body may include an apex 56 defining the maximum height of the prosthesis relative to the outer peripheral edge. The rounded ridge may include a first segment 58 extending from the first end 42 to the apex 56 and a second segment 60 extending from the second end 44 to the apex.

In one illustrative embodiment, the body may include a depression 62 configured to receive an adjacent vessel or organ when the prosthesis is implanted at the muscle or tissue wall. As illustrated, the depression 62 may be located along the second curved surface between the third and fourth portions 32, 34 of the body. The depression may extend across the second curved surface in a direction from the apex 56 toward the second margin 40. In one embodiment, the depression may be configured to receive the iliac vessels when the prosthesis is employed for inguinal hernia repair. However, it is to be understood that a depression is not required for all applications of the prosthesis. Moreover, a depression, if provided, may be configured to accommodate any vessel, organ, muscle or tissue which may be located adjacent the prosthesis when implanted at the defect site.

In one illustrative embodiment, the first portion 28 may have a spherical shape. As illustrated, the first portion is bounded by the first segment 46 of the first margin 38, the second portion 30, the first segment 58 of the rounded ridge 54 and a portion of the second segment 60 of the rounded ridge.

In one illustrative embodiment, the second portion 30 may have a conical shape with a base 64 extending from the first margin 38 to the rounded ridge 54 and a tip located at the second end 44 of the body. The second portion is joined to the first portion along its base and is bounded by the second segment 48 of the first margin and a portion of the second segment 60 of the rounded ridge.

In one illustrative embodiment, the third portion 32 may be joined to the first portion 28 along the first segment 58 of the rounded ridge between the first end 42 and the apex 56. The third portion may be joined to the fourth portion 34 along the depression 62 and is bounded by the first segment 50 of the second margin 40.

In one illustrative embodiment, the fourth portion 34 may be joined to the first and second portions 28, 30 along the second segment 60 of the rounded ridge 54 between the second end 44 and the apex 56. The fourth portion may be joined to the third portion 32 along the depression 62 and is bounded by the second segment 50 of the second margin 40 and the depression 62.

In one illustrative embodiment, the first curved surface formed by the first and second portions 28, 30 may have a first incline from the rounded ridge 54 to the first margin 38 and the second curved surface formed by the third and fourth portions 32, 34 may have a second incline from the rounded ridge 54 to the second margin 40. In one embodiment, the second incline may be greater than the first incline.

In one illustrative embodiment, the first and second margins 38, 40 of the body may be smooth and more rigid than the remainder of the body to facilitate the prosthesis. In this manner, the margins may be formed to facilitate the prosthesis independently returning to its preformed three-dimensional shape following collapse of the prosthesis. The margins may be formed by fusing the material over a width of approximately 3 mm. It is to be understood, however, that the width of the margins may be selected to vary its stiffness or rigidity.

For some applications, it may be desirable to employ a prosthesis configured to substantially reduce the incidence of wrinkles or folds between the first and second portions so that the first and second portions do not partially cover each other upon or after implantation, thereby ensuring that the overall size of the prosthesis is sufficient to adequately cover the desired portion of the wall. Such an arrangement may be particularly suited for a prosthesis having a relatively large size.

Figure 4:
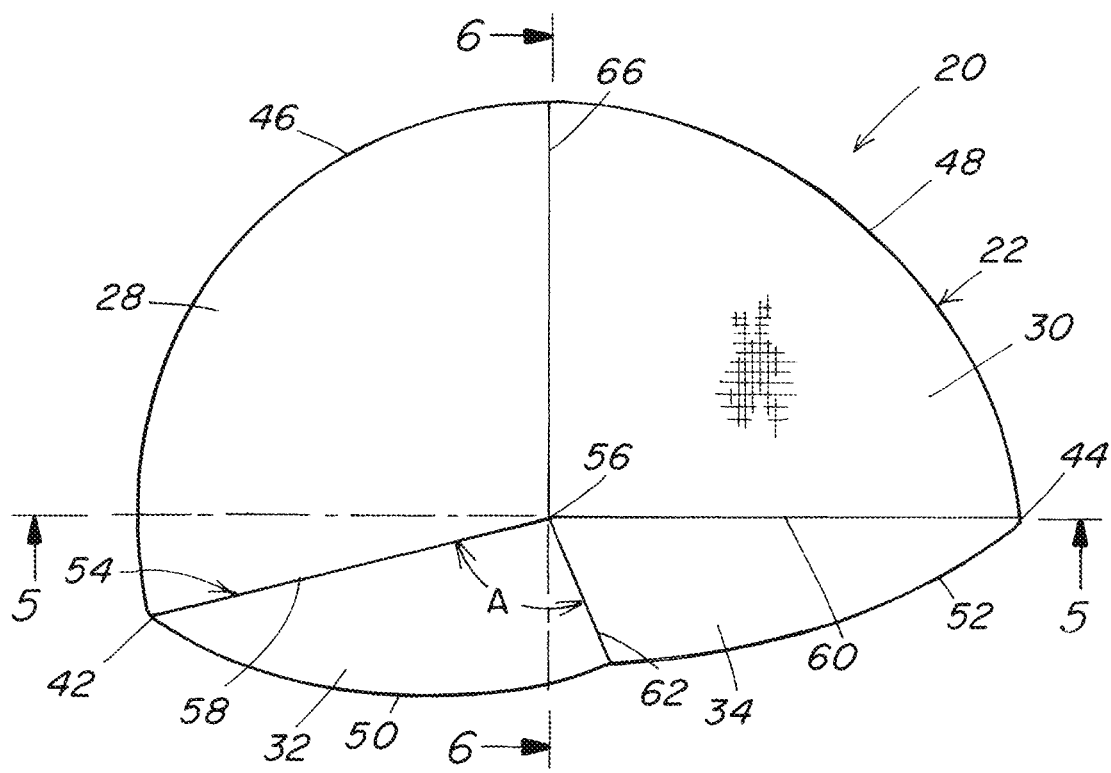
FIG. 4 is a plan view of a prosthesis according to another illustrative embodiment of the disclosure.

In one illustrative embodiment shown in FIGS. 4-6, the first portion 28 may have a spherical shape. As illustrated, the first portion is bounded by the first segment 46 of the first margin 38, the second portion 30 and the first segment 58 of the rounded ridge 54. The first segment 46 of the first margin 38 may have a circular shape. The boundaries 58, 66 of the first portion 28 with the second and third portions 30, 32 intersect each other at the apex 56 of the prosthesis.

In one illustrative embodiment, the second portion 30 merges with the first portion 28 along the boundary 66 and is bounded by the second segment 48 of the first margin and the second segment 60 of the rounded ridge 54. The second segment 48 of the first margin may have a circular shape.

In one illustrative embodiment, the first portion 28 has a first radius of curvature and the second portion 30 has a second radius of curvature that is substantially equal to the first radius of curvature along and perpendicular to the boundary 66 between the first and second portions. Such an arrangement may substantially reduce the incidence of wrinkles or folds between the first and second portions so that the first and second portions do not partially cover each other upon or after implantation, thereby ensuring that the overall size of the prosthesis is sufficient to adequately cover the desired portion of the wall.

In one illustrative embodiment, the third portion 32 merges with the first portion 28 along the first segment 58 of the rounded ridge 54 between the first end 42 and the apex 56. The third portion may be joined to the fourth portion 34 along the depression 62 and is bounded by the first segment 50 of the second margin 40. As illustrated, the first segment of the second margin may be curved.

In one illustrative embodiment, the fourth portion 34 merges with the second portion 30 along the second segment 60 of the rounded ridge 54 between the second end 44 and the apex 56. The fourth portion may be joined to the third portion 32 along the depression 62 and is bounded by the second segment 52 of the second margin 40 and the depression 62. As illustrated, the second segment of the second margin may be curved.

As illustrated in FIGS. 4-6, the first margin 38 and the second margin 40 form a generally D-shaped peripheral edge of the prosthesis. The peripheral edge may be welded or fused so that the body can regain its contoured shape after being deformed during implantation.

In one embodiment, each of the third and fourth portions 32, 34 may have substantially spherical shapes to enhance conformance to a particular anatomical shape. In one illustrative embodiment, the radius of curvature of the third and fourth portions 32, 34 is less than the radius of curvature of the first portion 28 to form surfaces in the third and fourth portions that have a steeper incline relative to the first portion.

The prosthesis may be configured to have any shape and size suitable for a particular application. In one embodiment, the height H of the prosthesis from a plane defined by the peripheral edge 36 and the apex 56 is approximately 21 mm. The first portion 28 has a substantially spherical shape with a radius of curvature of approximately 120 mm, particularly where it merges with the second portion 30 which has substantially the same radius of curvature of approximately 120 mm adjacent the first portion. The third and fourth portions 32, 34 each has a substantially spherical shape with a radius of curvature of approximately 35 mm. The total surface area of the prosthesis is approximately 44,780 mm$^2$, with the second portion 10 having a surface area of approximately 12,735 mm$^2$.

The illustrative embodiment is particularly suited for repairing an inguinal hernia. It is to be appreciated, however, that this configuration is exemplary and that the prosthesis may be configured to have other shapes and sizes suitable for a particular application.

As indicated above, it may be desirable to provide the prosthesis with a configuration particularly suitable for inguinal hernia repair. The prosthesis 20 may include a body 22 of prosthetic material that is preformed with a three-dimensional configuration that facilitates placement and minimize shifting of the prosthesis when positioned on the defective wall in the inguinal region. The body may include a plurality of shaped portions that together create a desired configuration. The particular orientation between several portions of the body may be configured to the inclination of the external iliac vessels and/or placement along the axis of the inguinal ligament to facilitate a desired placement of the prosthesis when employed for repairing an inguinal hernia.

In one embodiment shown in FIG. 4, the first and third portions 28, 32 may be configured with an angle A at the apex 56 between the first segment 58 of the rounded ridge 54 and the depression 62 which positions the depression substantially opposite the external iliac vessels when implanted to repair an inguinal hernia. In one embodiment, the angle A may be greater than 100°. In one embodiment, the angle A may have a range of approximately 101° to 120°. It is to be appreciated, however, that the prosthesis may employ other suitable angles A as should be understood to one of skill in the art to accommodate particular anatomical features.

The particular angular orientation between the first segment 58 of the rounded ridge 54 and the depression 62 between the third and fourth portions 32, 34 is adapted to the inclination of the external iliac vessels to facilitate placement of and to minimize shifting of the prosthesis when positioned on the wall. The angular orientation and the depression also provide a degree of deformation for matching adjacent contours.

For some applications, it may be desirable to provide one or more visual indicia to assist with placement and/or orientation of the prosthesis at the defect site.

Figure 7:
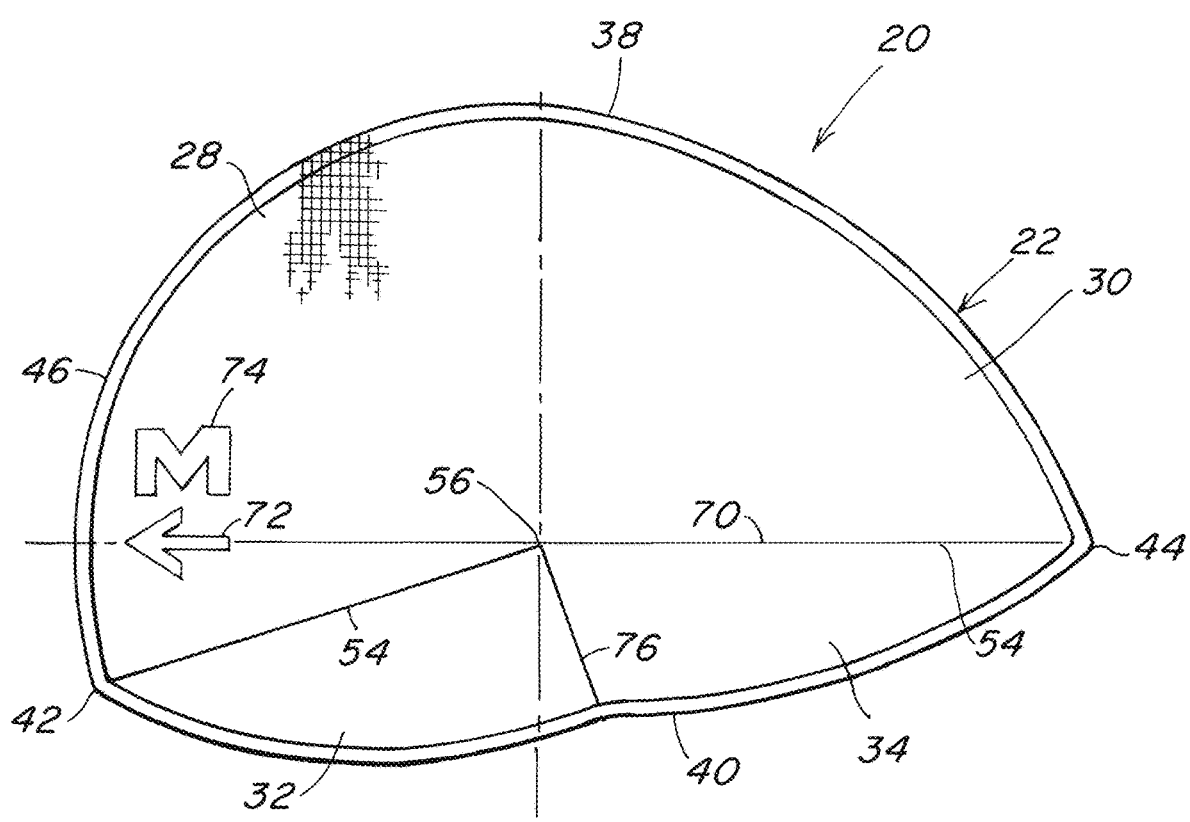
FIG. 7 is a plan view of the prosthesis of FIG. 4 illustrating positioning indicia according to one illustrative embodiment of the disclosure.

In one illustrative embodiment shown in FIGS. 2, 3 and 7, the prosthesis may include a first indicia 70 which extends along the rounded ridge 54 between the second end 44 and the apex 56. As illustrated, the first indicia 70 may extend through the apex and across the first portion 28 toward a location along the first segment 46 of the first margin 38 offset from the first end 42. For inguinal hernia repair, the first indicia 70 may be arranged to facilitate placement and orientation of the prosthesis along the inguinal ligament.

One or more additional symbols may be provided to assist with placement and orientation of the prosthesis. As illustrated, an arrow symbol 72, along with an alphabetic symbol "M" 74, may be provided to visually identify the medial portion of the prosthesis which is to be placed at the medial end of the inguinal canal. It is to be appreciated that any one or more suitable symbols, if desired, may be employed to assist with placement and orientation of the prosthesis.

In one illustrative embodiment shown in FIGS. 2, 3 and 7, a second indicia 76 may be provided to assist with identifying the depression 62 of the prosthesis. The second indicia 76 may extend along the depression between the second margin 40 and the apex 56. As illustrated, the indicia may extend from the apex and between the third and fourth portions 32, 34 of the body. For inguinal hernia repair, the second indicia 76 may be arranged to facilitate placement and orientation of the depression adjacent the iliac vessels.

In one illustrative embodiment, the first and second indicia 70, 76 may extend across the body 22 in a linear direction. It is to be appreciated, however, that the indicia may have any suitable configuration as should be understood by one of skill in the art.

In one embodiment, the indicia may be formed with a monofilament which may be stitched on or knitted into the body. The indicia may have a contrasting color relative to the body to assist with readily identifying the indicia. It is to be appreciated that the visual indicia may be formed on the body using any suitable technique, such as printing or stenciling, as should be apparent to one of skill in the art.

The body 22 of the prosthesis 20 may include a mesh fabric employing a knit construction that provides relatively large openings or pores to ensure good visibility of the underlying anatomy without sacrificing mechanical properties of the mesh. The porous character of the fabric allows tissue infiltration to incorporate the prosthetic. The knitted fabric is sufficiently strong and structured to prevent or minimize potential pullout of anchoring fasteners, such as sutures, staples, tacks, and the like. The repair fabric may have flexibility sufficient to promote an easy reduction in size for entry into the subject. In this manner, the flexible fabric may be collapsed into a slender configuration, such as a roll, which can be supported in, and advanced through, a narrow laparoscopic cannula for use in laparoscopic procedures.

The mesh fabric may employ a relatively lighter weight, thinner, and/or more flexible fabric construction that may introduce less foreign body material into a patient as compared to other repair fabrics. The porous prosthetic repair fabric allows a prompt fibroblastic response through the interstices of the mesh, forming a secure fibrous/prosthetic layer. The fabric may promote a thinner and more compliant scar plate that may result in a relatively more comfortable soft tissue or muscle wall repair for a patient.

Figure 8:
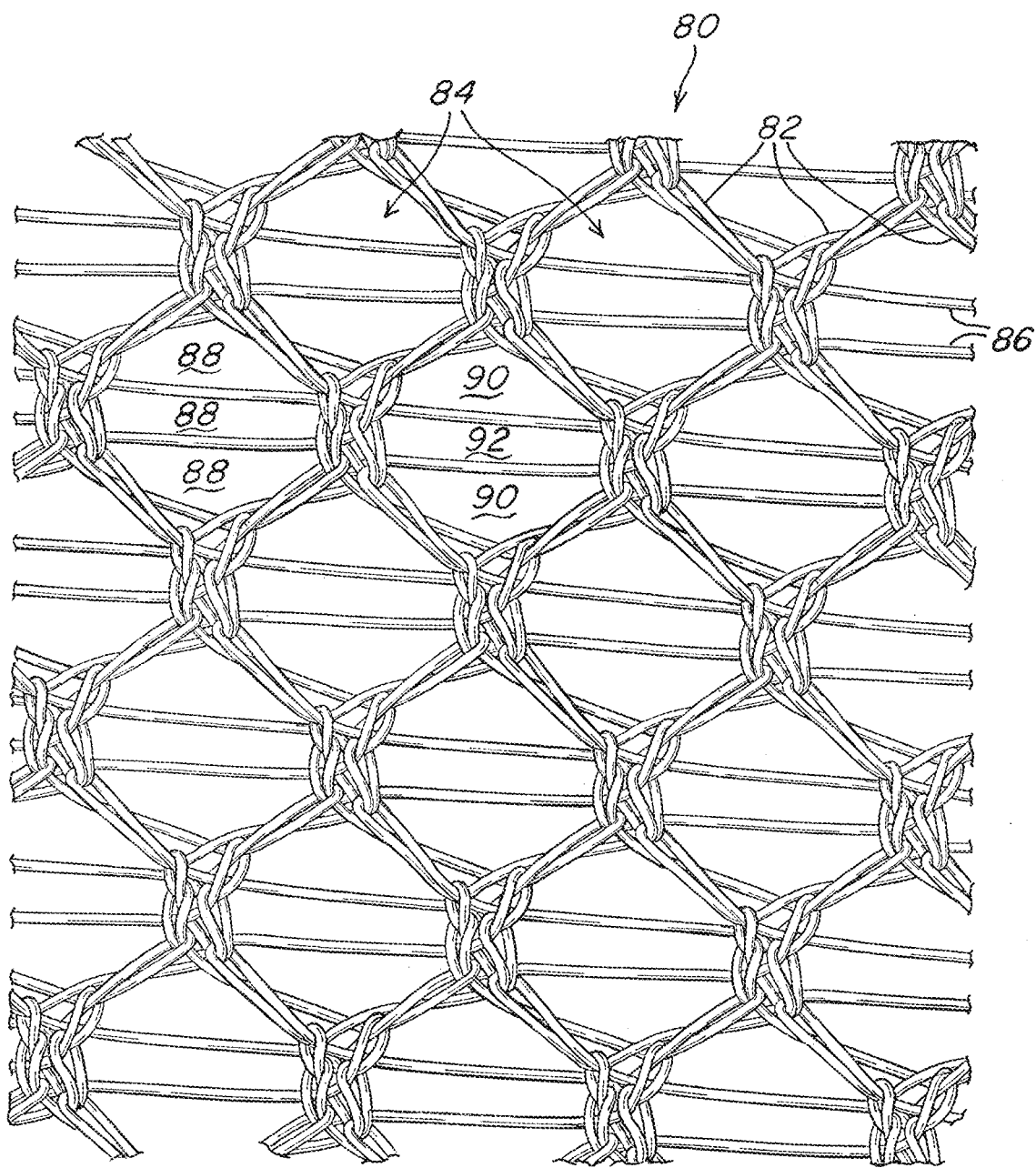
FIG. 8 is an enlarged view of a dual bar warp knit, mesh fabric according to an illustrative embodiment of the present disclosure.

In one illustrative embodiment shown in FIG. 8, the repair fabric may comprise a knit mesh 80 including knitted strands of filaments 82 that define larger, primary pores 84 arranged in a uniform pattern. A pair of individual filaments 86 extend across the primary pores to define a plurality of smaller, secondary pores 88 therein.

In the illustrated embodiment, the primary pores 84 are bounded by knitted strands of filaments 82. However, it is to be appreciated that one of more boundaries of the primary pores 84 may be defined by individual filaments as would be apparent to one of skill in the art. As shown, the primary pores 84 may have a generally polygon shape, such as hexagon, diamond or square shaped, although aspects of the disclosure are not limited. In this regard, it is to be understood that other pore shapes are also contemplated, including, but not limited to, circular, non-circular, round, oval and the like, as would be apparent to one of skill in the art.

The prosthetic repair fabric may be constructed to increase flexibility and/or reduce the overall weight per unit area of the fabric. Such properties may facilitate an easier collapse of the repair fabric for introduction into a patient. These properties may also provide for easier manipulation of the repair fabric about the surgical site within the patient. In one illustrative embodiment, the primary pores 84 have an area of approximately 0.01032 to 0.01233 square inches prior to the mesh being formed into a three-dimensional contoured configuration. In this regard, less material may be used to produce a given area of mesh, which may result in a reduced weight mesh. Additionally, the generally greater spacing between the strands of filaments 82 that are associated with the larger primary pores 84 may also contribute to a more flexible mesh. It is to be appreciated, however, that the size of the primary pores may vary as would be apparent to one of skill in the art, as aspects of the disclosure are not limited in this respect.

For some applications, it may be desirable to provide secondary pores 88 within the primary pores 84. In one illustrative embodiment shown in FIG. 8, each primary pore 84 is subdivided into a plurality of secondary pores 88 by a pair of individual or single filaments 86. In the illustrative embodiment, the pair of filaments 86 divides the primary pore 84 into a pair of generally triangular secondary 90 pores and a generally rectangular secondary pore 92 that is positioned between the two generally triangular secondary pores 90. It is to be appreciated, however, that the shapes of secondary pores and/or numbers of secondary pores within each primary pore, if desired, may vary as would be apparent to one of skill in the art, as aspects of the disclosure are not limited in this respect.

In one illustrative embodiment as shown in FIG. 8, the pair of individual filaments 86 extend substantially parallel to one another across the primary pores 84. As illustrated, the pair of parallel filaments 86 may be generally in linear alignment with corresponding pairs of filaments in adjacent primary pores. However, it is to be understood that the individual filaments may be positioned and oriented in other suitable arrangements, as aspects of the present disclosure are not limited in this respect.

The prosthetic repair fabric may be constructed so as to be provisionally anchored to tissue or muscle using a wide variety of fasteners, such as sutures, staples, spiral tacks, Q-rings and the like. The individual filaments 86 that extend across the primary pores may provide additional features for engaging the fasteners used to anchor the fabric. It is to be appreciated that repair fabrics may be anchored to tissue and/or mesh with fasteners, such as spiral tacks and Q-ring constructs, that have relatively small features for engaging and holding the repair fabric in place. The smaller, secondary pores 88 associated with the individual filaments may provide for improved engagement with the fasteners in a manner that is sufficiently strong and structured to prevent or minimize pullout. It is to be appreciated that the size of the secondary pores may vary as would be apparent to one of skill in the art, as aspects of the disclosure are not limited in this respect.

The knit mesh may employ filaments having the same size or different relative sizes to adjust mechanical properties of the fabric. In one illustrative embodiment, the mesh fabric may include first filaments 82 having a first diameter to form the primary pores and second filaments 86 having a second diameter that is different from the first diameter extending across the primary pores. In one embodiment, the second filaments 86 have a second diameter that is greater than the first diameter of the first filaments. Such an arrangement may enhance the handling of the mesh fabric by increasing its stiffness. It is to be appreciated, however, that other arrangement are contemplated. For example, and without limitation, the diameter of the first filaments 82 may be greater than the diameter of the second filaments 86.

In one illustrative embodiment, the knit mesh 80 may be produced in a lapping pattern by using two partially threaded guide bars to knit the pattern over three needles in a six course repeat. The fabric structure may be of an atlas type where each knitted end travels more than two needles, which may prevent unraveling of the mesh.

Figure 9A:
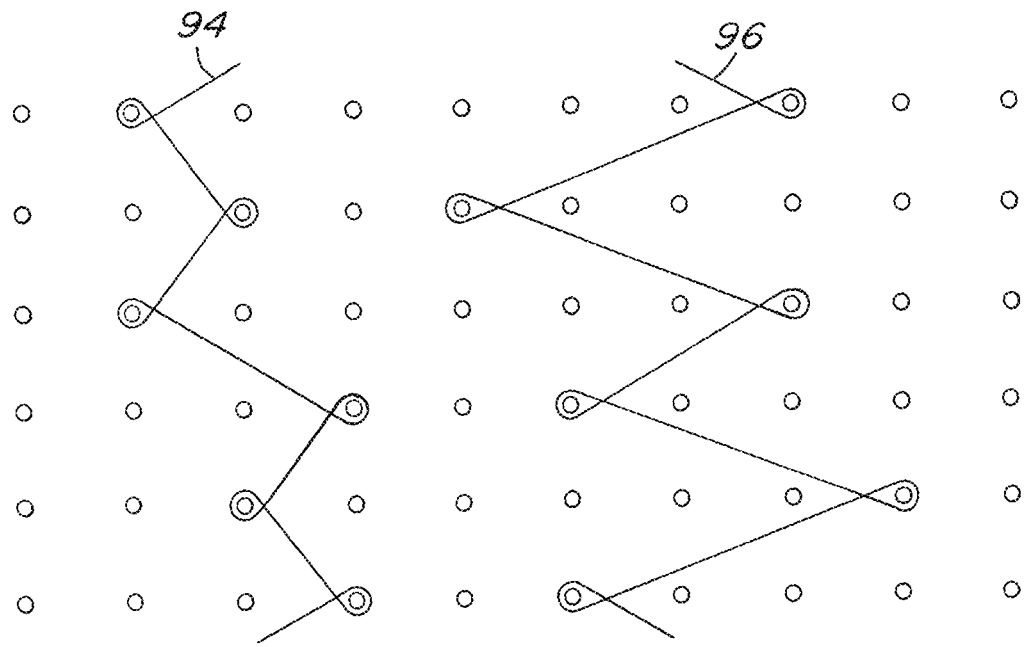
FIGS. 9A-9B illustrate the chain lapping pattern for the mesh fabric of FIG. 8.
Figure 9B:
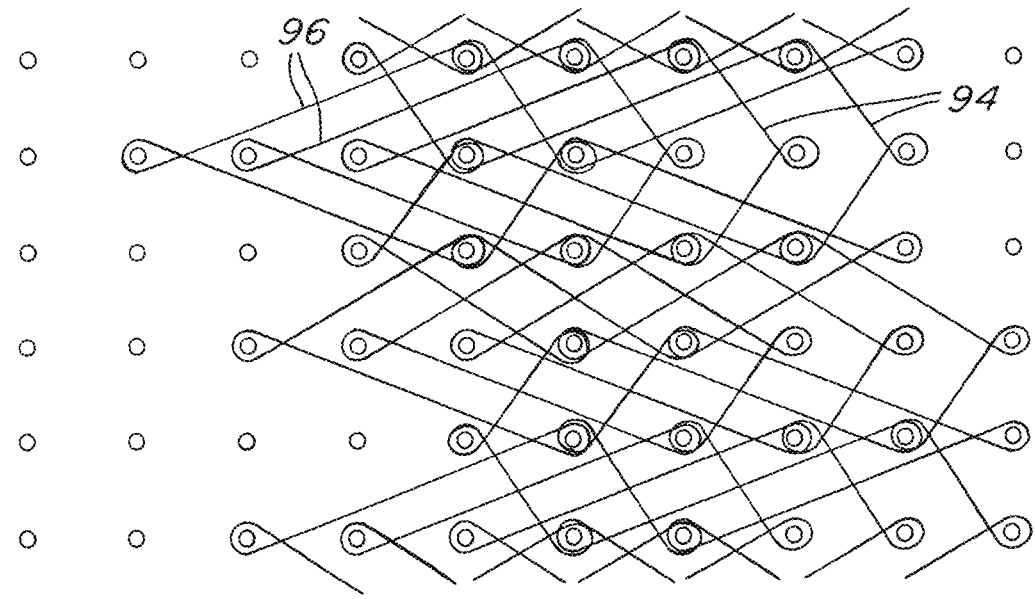

In one illustrative embodiment shown in FIGS. 9A-9B, the repair fabric may employ a dual bar warp knit mesh structure produced using two guide bars moving according to a first bar pattern chain of 4/2 4/6 4/2 6/8 6/4 6/8 (identified as reference 94) and a second bar pattern chain of 6/8 2/0 6/8 4/2 8/10 4/2 (identified as reference 96). The mesh may be knitted on a single needle bar, 24 gauge Rachelle knitting machine. The mesh may be fabricated with approximately 34 to 36 courses per inch and approximately 12 to 17 wales per inch. It is to be appreciated, however, that the mesh fabric may be knitted using any suitable knit pattern as would be apparent to one of skill in the art, as aspects of the disclosure are not limited in this respect.

The knit mesh may be produced at various widths apparent to one of skill in the art, such as from 1 inch to 80 inches, depending on the intended application for which the repair fabric is being produced.

Following knitting, the fabric may be washed to remove foreign matter, such as residual processing lubricant. A cleaning agent, such as Triton X-100, may be used to aid in the removal of such foreign matter. Following washing, the mesh may be dried at a temperature lower than the heat set and melt temperatures of the material, as would be apparent to one of skill in the art.

Embodiments of the knit mesh may be heat set to impart a shape memory to the mesh and the prosthetic fabric formed of the mesh. In one illustrative embodiment, the fabric is heat set to have a generally planar shape memory. In this manner, after the fabric is collapsed and inserted into a patient, the fabric may revert back to the planar configuration for appropriate placement against tissue of the patient. It is to be appreciated that other embodiments of the fabric may be provided with a shape memory that corresponds to configurations different than planar, or to have no shape memory at all, as aspects of the disclosure are not limited in this regard.

If desired, the knit mesh may be heat set under tension, in a crochet hoop or tentering frame. The heat set may be applied while the mesh knit is being stretched in a particular direction to help set the mesh into a particular configuration. In one illustrative embodiment, the knit mesh is stretched in the cross machine knit direction and simultaneously allowed to partially relax or contract in the machine direction to a fixed point while heat is applied to set the mesh. It is to be understood, however, that other techniques apparent to one of skill in the art may be used to heat set the knit mesh, as aspects of the disclosure are not limited in this respect.

For some applications, it may be desirable to smooth the knitted mesh to reduce the texture or surface roughness of the mesh. In one illustrative embodiment, the knitted mesh is lightly pressed between a pair of plates which includes a heated plate that is pressed against the rough surface of the mesh to reduce high spots of the mesh and to heat set it to smooth its surface. It is to be appreciated, however, that the fabric may be smoothed using any suitable process apparent to one of skill in the art. For example, the fabric may be smoothed by passing the knitted mesh between a pair of heated rollers during the washing and drying process.

The filaments that are used to fabricate the repair fabric may contribute to the resulting mechanical properties of the fabric. In one illustrative embodiment, the repair fabric is knitted with first filaments having a diameter of approximately 0.0045 to 0.0051 inches (first bar pattern chain), and preferably a diameter of approximately 0.0048 inches, and second filaments having a diameter of approximately 0.0063 to 0.0075 inches (second bar pattern chain), and preferably a diameter of approximately 0.0075 inches. Filaments of these diameters may contribute to an increased flexibility and reduced weight per unit area of the overall repair fabric. It is to be understood, however, that the fabric may be fabricated with filaments having any suitable diameter apparent to one of skill in the art that is suitable for a desired application, as aspects of the disclosure are not limited in this respect.

In one illustrative embodiment, the fabric has a thickness of approximately 0.022 to 0.024 inches, and preferably a thickness of approximately 0.0225 to 0.0235 inches. In one illustrative embodiment, the fabric has a weight per unit area of approximately 0.066 to 0.069 grams per square inch. It is to be appreciated, however, that the fabric may be fabricated to have any thickness and/or weight per unit area apparent to one of skill in the art that is suitable for a desired application, as aspects of the disclosure are not limited in this respect.

In one illustrative embodiment, the filaments used to fabricate the mesh fabric comprise a polypropylene monofilament, which is inert in the presence of infection, is non-wettable and has a low foreign body reaction. In one illustrative embodiment, the monofilaments are formed of Aran Biomedical ProTex Med Polypropylene resin PPS50156 and PPS50157. In one embodiment, the first has a denier of approximately 98±11 and the second monofilament has a denier of approximately 240±20. In one embodiment, the first and second monofilaments have a tenacity of approximately 6.0 to 8.5 grams/denier, with a nominal tenacity of approximately 6.2 grams/denier. It is to be appreciated, however, that filaments of different configurations, properties and/or materials may be employed to fabricate the fabric. For example, the filaments may comprise multifilaments or monofilaments having different mechanical characteristics as would be apparent to one of skill in the art, as aspects of the present disclosure are not limited in this respect.

The preformed curved shape of the prosthesis may be obtained using any suitable manufacturing process. In one illustrative embodiment shown in FIG. 8, the prosthesis is fabricated using a thermoforming procedure that includes placing a sheet of mesh fabric in a mold having the desired shape for the prosthesis, heating the fabric in the mold at an approximate temperature of 100° C. to 200° C. for a period of approximately 5 to 60 minutes, and subsequently cooling the fabric in the mold with an air flow having an approximate temperature of 15° C. to 30° C. for a period of approximately 5 to 60 minutes.

The edges of the prosthesis may be welded by fusing the material using an ultrasonic welding procedure. During this procedure, the prosthesis may be maintained between an element generating vibrations and an anvil that is configured to the particular dimensions of the prosthesis. In one embodiment, the edges are welded at a pressure of approximately 150 kPa to 800 kPa and an energy of approximately 100 to 5000 joules for a period of approximately 50 to 5000 milliseconds.

Once the sheet of mesh fabric has been shaped and the edges of the shaped prosthesis have been welded, any excess fabric extending beyond the welded edges is separated from the body of the prosthesis using a manual cutting procedure to form the completed prosthesis.

Following inspection, the prosthesis may be packed in an internal packing (shell and insert) that has been designed specifically according to the three-dimensional characteristics of the prosthesis so as to comply with and protect the preformed curved shape of the prosthesis. The internal packing may be subsequently placed and packaged in a external packing for additional protection. The entire assembly may then be sterilized using any suitable method, such as with ethylene oxide, to provide a sterile prosthesis that is ready for implantation.

EXAMPLES

The following examples are illustrative only and are not intended to limit the scope of the present disclosure.

Physical properties of a representative preformed three-dimensional contoured prosthesis fabricated from a two bar warp knit mesh fabric produced from 0.0048 inch (first bar) and 0.0075 inch (second bar) polypropylene monofilament according to the illustrative embodiments shown in the figures (labeled Embodiment #1 in Table 1) were evaluated and compared to a known preformed three-dimensional contoured prosthesis (comparative prosthesis). Physical and performance characteristics were tested including mesh thickness, pore size, mesh weight per unit area, suture pull out strength, burst strength, tear resistance, tensile (break) strength and elongation at break, and stiffness. Testing methodology and results appear below in Table 1, where mean results and ranges are reported from several test samples (ranges appear in parentheses).

Suture Pullout Strength:

A sample of mesh measuring at least 1 inch×1 inch (Embodiment #1) or at least 0.5 inch×3 inches (comparative mesh fabrics) was prepared from preformed prostheses and clamped in the lower jaw of an MTS™ or equivalent tensile test machine. The long dimension of the sample should be parallel with its orientation designation (machine or cross-machine). At least 0.5 inch (Embodiment #1) or at least 1 inch (comparative prosthesis) of the mesh was exposed above the jaw. A spring steel wire with a diameter of approximately 0.019 inches was placed through the mesh to simulate a suture. The wire was placed 5±1 mm from the edge of the mesh. The wire suture was looped back and both ends were attached to the upper jaw of the tensile machine. The suture was then pulled at a rate of 5 inches per minute through the mesh. The peak force was recorded for samples tested in both the machine and cross directions of the mesh and the average force was calculated for the total measurements in each direction.

Pore Size:

A sample of mesh from preformed prostheses was placed on an optical coordinate measurement device such as a Tesa Vision (35×) or equivalent.

Figure 10:
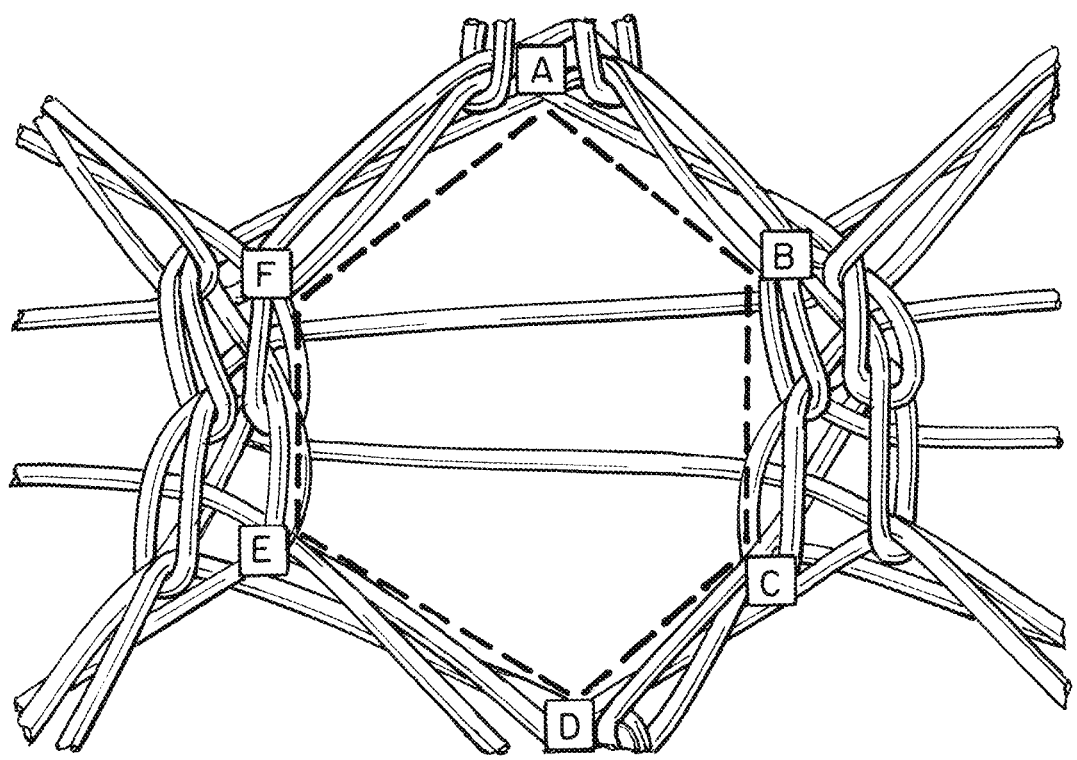
FIG. 10 is a schematic illustration for determining the area of a primary cell.

For embodiment #1, each primary pore has a generally hexagon shape which contains two generally triangular pores and a generally rectangular pore in the middle section. The length L of each leg of the primary pore was measured dimensionally between each pair of end points A-B, B-C, C-D, D-E, E-F and F-A, as illustrated by dashed lines in FIG. 10. The pore area of the primary pore was calculated based on the area of a hexagon as follows, where $L_{average}$ is the average length of each leg:

$$\text{Area} = (L_{average})^2 \times (3\sqrt{3})/2$$

Randomly selected primary cells (not counting the pores formed by the loops or knots) of each sample were measured and a combined average was calculated.

Tensile (Break) Strength and Elongation at Break:

A mesh sample measuring approximately 1 inch×6 inches from preformed prostheses was placed into the pneumatic jaws of an MTS™ tensile tester or equivalent device. The sample was oriented so that the knit direction being tested was parallel to the 6 inch length. The ends of the 6 inch sample were gripped in the lower and upper jaws of the tester. Starting with a minimum separation of 2 inches, the sample was pulled at a constant rate of 12 inches per minute until the sample broke. The peak load and elongation at break were recorded. The samples were tested in both the cross direction and the machine direction. The averages of the measurements taken from the samples were then calculated for each direction.

Mesh Thickness:

A sample of mesh from preformed prostheses was measured using a standard thickness snap gage with an approximate 0.38 inch diameter pressure foot that is lightly spring loaded. The thickness was measured by lowering the foot onto the mesh. Measurements were taken to the nearest 0.0001 inch. A combined average was calculated for the total number of measured mesh.

Mesh Weight/Unit Area:

Using a sample size of multiple pieces of mesh that measured at least approximately 2 inches×2 inches from preformed prostheses, the weight of each sample was measured in grams to the nearest 0.0001 gram. The area was calculated by measuring the length and width dimensions taken to the nearest 0.001 inch, minus the area of any radiused corner. The weight per unit area was calculated for each sample using the weight and unit area. The average weight per unit area was calculated by combining and averaging the weight per unit area for each sample.

Burst Strength:

This test method was derived from the ANSI/AAMI VP20-1994 Section 8.3.3.2 and ASTM Ball Burst method D3787-01. A mesh sample from preformed prostheses was placed on top of a circular O-ring measuring approximately 1 inch in diameter. The O-ring was seated in a grooved plate in a fixture with a hole in the middle of plate containing the O-ring. The fixture was attached to the lower jaw in an MTS™ or equivalent test machine. The plate with the mesh was raised and clamped against an upper plate in the fixture, compressing the mesh sample. The upper plate also contained a hole with the same diameter as the lower plate. The holes in the fixture plates are dimensioned to be just slightly larger than and to accept a rounded ball tipped rod that has a 0.38 inch diameter tip. The rod was connected to an upper jaw of the test machine that was moved down through the sample at a constant rate of 12 inches per minute. The peak load was recorded for the samples and the average burst strength was then calculated based on the peak loads for the samples.

Tear Resistance:

A mesh sample measuring approximately 2 inches×2 inches was prepared from preformed prostheses. A 1 inch slit was cut in one side (the direction to be tested) at the midpoint to form two mesh sections. One section of mesh was clamped in the lower jaw of a pneumatic fixture and the other was clamped in the top jaw of the fixture. Starting with the jaws at a minimum spacing of 1 inch, the mesh was pulled at a rate of 12 inches per minute until the tear was completed. The peak force was recorded. Samples were tested in the cross direction and the machine direction (Embodiment #1), and the cross direction, the machine direction, and the diagonal direction (comparative mesh fabrics). The averages of the total measurements taken from the samples were then calculated for each group direction.

Stiffness:

The stiffness test was based on the stiffness of a fabric by a circular bend procedure (see ASTM Standard D4032-08 (2016)). A preformed three-dimensional anatomically shaped prosthesis was placed on top of a plate with the dome of the shaped mesh facing down. The mesh was centered over an orifice in the plate. The orifice has a 1.5 inch diameter with a chamfered lead-in. The mesh was pushed or plunged down into this plate by a 1 inch diameter plunger. The plunger was set to travel at a constant rate of 12 inches per minute. The plunger traveled 1.5 inches below the top surface of the orifice platform and the peak load was recorded. The samples were tested and the average was calculated for the entire group.

TABLE I

| | Embodiment #1 | BARD 3DMax Light |
|---|---|---|
| Suture Pullout (lbs) | | |
| Machine Direction | 10.2 (6.9 to 12.4) | 9.6 |
| Cross Direction | 8.5 (7.7 to 13.7) | 10.3 |
| Pore Size (inches²) | | |
| Large Cell | 0.0082 (0.0079 to 0.0087) | 0.0101 |
| Tensile (Break) Strength (lbs) | | |
| Machine Direction | 14.8 (12.6 to 17.1) | 11.2 |
| Cross Direction | 39.6 (31.4 to 44.9) | 25.1 |
| Elongation at Break (%) | | |
| Machine Direction | 113.2 (100.3-133.7) | 52.9 |
| Cross Direction | 60.3 (52.6-66.4) | 36.2 |
| Mesh Thickness (Inches) | | |
| | 0.027 (0.025-0.028) | 0.021 |
| Weight/Unit Area (gms/inches²) | | |
| | 0.0504 (0.0491-0.0517) | 0.0272 |
| Tear Resistance (lbs) | | |
| Machine Direction | 9.6 (7.8-12.3) | 5.99 |
| Cross Direction | 10.4 (7.7-12.9) | 6.05 |
| Stiffness (lbsf) | | |
| | 1.054 | 0.505 |
| Ball Burst (⅜" ball, lbs) | | |
| | 48.8 (45.7-51.6) | 28.1 |
| Mesh Construction | | |
| Courses (per inch) | 30 | 23.4 |
| Wales (per inch) | 12 | 16 |

It should be understood that the foregoing description of the disclosure is intended merely to be illustrative thereof and that other equivalents, embodiments and modifications of the disclosure are within the scope of the disclosure recited in the claims appended hereto.

What is claimed is:

1. An implantable prosthesis for repairing an inguinal hernia, the prosthesis comprising:
a body of biologically compatible prosthetic material having a preformed three-dimensional contoured shape that independently assumes a curved shape configured to conform to the inguinal wall, the body being surrounded by an outer peripheral edge and including an apex relative to the outer peripheral edge, the body including a depression configured to receive external iliac vessels, the depression extending in a first direction from the apex toward the outer peripheral edge, the body including a first visual indicia extending in the first direction along at least a portion of the depression between the apex and the outer peripheral edge, the first visual indicia having a contrasting color relative to the body.

2. The implantable prosthesis according to claim 1, wherein the first visual indicia extends from the apex.

3. The implantable prosthesis according to claim 1, wherein the first visual indicia includes a line extending along the depression.

4. The implantable prosthesis according to claim 1, wherein the outer peripheral edge defines a first plane, the first visual indicia extending in a second plane positioned transverse to the first plane.

5. The implantable prosthesis according to claim 1, wherein the body includes a rounded ridge extending in a second direction from the outer peripheral edge to at least the apex, the rounded ridge configured to be placed along the axis of the inguinal ligament, the body including a second visual indicia extending in the second direction along at least a portion of the rounded ridge between the outer peripheral edge and the apex, the second visual indicia having a contrasting color relative to the body.

6. The implantable prosthesis according to claim 5, wherein the second visual indicia extends through the apex.

7. The implantable prosthesis according to claim 6, wherein the second visual indicia includes a line extending across the body.

8. The implantable prosthesis according to claim 5, wherein the first visual indicia extends in a first direction and the second visual indicia extends in a second direction transverse to the first direction.

9. The implantable prosthesis according to claim 1, wherein the body includes a convex outer surface and a concave inner surface.

10. An implantable prosthesis for repairing an inguinal hernia, the prosthesis comprising:
a body of biologically compatible prosthetic material having a preformed three-dimensional contoured shape that independently assumes a curved shape configured to conform to the inguinal wall, the body being surrounded by an outer peripheral edge and including an apex relative to the outer peripheral edge, the body including a rounded ridge extending in a first direction from the outer peripheral edge to at least the apex, the rounded ridge being configured to be placed along the axis of the inguinal ligament, the body including a first visual indicia extending in the first direction along at least a portion of the rounded ridge between the outer peripheral edge and the apex, the first visual indicia having a contrasting color relative to the body.

11. The implantable prosthesis according to claim 10, wherein the first visual indicia extends from the apex.

12. The implantable prosthesis according to claim 10, wherein the first visual indicia extends through the apex.

13. The implantable prosthesis according to claim 10, wherein the first visual indicia includes a line extending across the body.

14. The implantable prosthesis according to claim 10, wherein the outer peripheral edge defines a first plane, the first visual indicia extending in a second plane positioned transverse to the first plane.

15. The implantable prosthesis according to claim 10, wherein the body includes a first curved surface and a second curved surface, the rounded ridge located between the first curved surface and the second curved surface, the second surface being steeper than the first curved surface relative to the outer peripheral edge.

16. The implantable prosthesis according to claim 10, wherein the body includes a convex outer surface and a concave inner surface.

\* \* \* \* \*